(12) United States Patent
Ben Ayad et al.

(10) Patent No.: US 8,759,343 B2
(45) Date of Patent: Jun. 24, 2014

(54) AZABICYCLOALKANE DERIVATIVES, PREPARATION THEREOF AND USE THEREOF IN THERAPY

(75) Inventors: Omar Ben Ayad, Villeneuve la Garenne (FR); Odile LeClerc, Massy (FR); Alistair Lochead, Charenton le Pont (FR); Mourad Saady, Paris (FR); Franck Slowinski, Le Plessis Robinson (FR); Julien Vache, Paris (FR)

(73) Assignee: Sanofi, Paris (FR)

( * ) Notice: Subject to any disclaimer, the term of this patent is extended or adjusted under 35 U.S.C. 154(b) by 113 days.

(21) Appl. No.: 13/422,296

(22) Filed: Mar. 16, 2012

(65) Prior Publication Data

US 2012/0202807 A1 Aug. 9, 2012

Related U.S. Application Data

(63) Continuation of application No. 12/535,156, filed on Aug. 4, 2009, now Pat. No. 8,173,669, which is a continuation of application No. PCT/FR2008/000137, filed on Feb. 4, 2008.

(30) Foreign Application Priority Data

Feb. 9, 2007 (FR) ..................... 07 00940

(51) Int. Cl.
| | | |
|---|---|---|
| *A61K 31/4439* | (2006.01) | |
| *C07D 401/14* | (2006.01) | |
| *C07D 413/14* | (2006.01) | |
| *C07D 401/04* | (2006.01) | |
| *A61K 31/496* | (2006.01) | |
| *A61K 31/506* | (2006.01) | |
| *A61K 31/5377* | (2006.01) | |

(52) U.S. Cl.
USPC ............... 514/233.2; 514/339; 514/253.09; 514/256; 546/276.7; 544/333; 544/122

(58) Field of Classification Search
USPC .............. 514/233.2, 339, 253.09, 256; 546/276.7; 544/364, 333, 122
See application file for complete search history.

(56) References Cited

FOREIGN PATENT DOCUMENTS

| | | |
|---|---|---|
| WO | WO 95/03306 | 2/1995 |
| WO | WO 03/057697 | 7/2003 |
| WO | WO 2004/111031 | 12/2004 |
| WO | WO 2007/020344 | 2/2007 |

OTHER PUBLICATIONS

Buckingham et al., Pharmacological review, 61:39-61, 2009.*
Anderson, D. J., et. al., Nicotinic Receptor Binding of [3H]Cytisine, [3H]Nicotine and [3H]Methylcarbamylcholine in Rat Brain, European Journal of Pharmacology, vol. 253, (1994), pp. 261-267.
Houghtling, R. A, et. al., Characterization of (+)-[3H]Epibatidine Binding to Nicotinic Cholinergic Receptors in Rat and Human Brain, Mol. Pharmacology, (1995), vol. 48, pp. 280-287.
Marks, M. J., et. al., Nicotinic Binding Sites in Rat and Mouse Brain: Comparison of Acetyicholine, Nicotine, and a-Bungarotoxin, Mol. Pharmacology, (1986), vol. 30, pp. 427-436.
International Search Report for WO2008/110699 dated Sep. 18, 2008.

* cited by examiner

*Primary Examiner* — Niloofar Rahmani
(74) *Attorney, Agent, or Firm* — Scully, Scott, Murphy & Presser, P.C.

(57) ABSTRACT

The invention relates to compounds of the general formula (I):

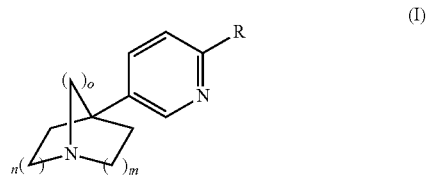

wherein R, m, n and o are as defined herein. The invention also relates to a method for preparing the same and to the application in therapy.

8 Claims, No Drawings

# AZABICYCLOALKANE DERIVATIVES, PREPARATION THEREOF AND USE THEREOF IN THERAPY

This application is a continuation of U.S. application Ser. No. 12/535,156, filed Aug. 4, 2009, now allowed, which is a continuation of International application No. PCT/FR2008/000137, filed Feb. 4, 2008, which are incorporated herein by reference in their entirety; which claims the benefit of priority of French Patent Application No. 0700940, filed Feb. 9, 2007.

The present invention relates to azabicycloalkane derivatives, to their preparation and to their therapeutic application.

The document WO03/057697A describes 5-(pyridin-3-yl)-1-azabicyclo[3.2.1]octane derivatives which are ligands of nicotinic receptors and which are of use in the treatment or prevention of disorders related to dysfunctioning of nicotinic receptors, in particular in the central nervous system.

There still exists a need to find and develop improved products for nicotinic receptors.

The invention meets this aim by providing novel compounds which exhibit an affinity for nicotinic receptors.

A subject-matter of the present invention is the compounds corresponding to the general formula (I)

(I)

in which:
R represents
either a hydrogen or halogen atom;
or a hydroxyl, ($C_1$-$C_6$)alkoxy, ($C_3$-$C_7$)cycloalkyl-O— or ($C_3$-$C_7$)cycloalkyl-($C_1$-$C_3$)alkylene-O— group;
or a heterocycloalkyl, aryl or heteroaryl group; it being possible for this group optionally to be substituted by one or more groups chosen from halogen atoms or ($C_1$-$C_6$)alkyl, ($C_3$-$C_7$)cycloalkyl, ($C_3$-$C_7$)cycloalkyl-($C_1$-$C_3$)alkylene, ($C_1$-$C_6$)alkoxy, ($C_3$-$C_7$)cycloalkyl-O—, ($C_3$-$C_7$)cycloalkyl-($C_1$-$C_3$)alkylene-O—, ($C_1$-$C_6$)fluoroalkyl, ($C_1$-$C_6$)fluoroalkoxy, nitro, cyano, hydroxyl, amino, ($C_1$-$C_6$)alkylamino or di($C_1$-$C_6$)alkylamino, heterocycloalkyl, aryl, aryl-($C_1$-$C_6$)alkylene, heteroaryl, heteroaryl-($C_1$-$C_6$)alkylene, aryl-O— or —C(O)—($C_1$-$C_6$)alkyl groups, the heterocycloalkyl group optionally being substituted by —C(O)O(CH$_3$)$_3$;
n represents 1 or 2;
m represents 1 or 2;
o represents 1 or 2;
the case where n and o=1 and m=2 being excluded;
the following compounds being excluded:
4-(6-fluoropyridin-3-yl)-1-azabicyclo[2.2.1]heptane;
4-(6-chloropyridin-3-yl)-1-azabicyclo[2.2.1]heptane;
4-(6-bromopyridin-3-yl)-1-azabicyclo[2.2.1]heptane;
4-(pyridin-3-yl)-1-azabicyclo[2.2.1]heptane.

4-(6-Fluoropyridin-3-yl)-1-azabicyclo[2.2.1]heptane, 4-(6-chloropyridin-3-yl)-1-azabicyclo[2.2.1]heptane, 4-(6-bromopyridin-3-yl)-1-azabicyclo[2.2.1]heptane and 4-(pyridin-3-yl)-1-azabicyclo[2.2.1]heptane are described in the document WO95/03306A as arthropodicidal compounds.

The compounds of formula (I) can comprise one or more stereogenic centers, such as, for example, one or more asymmetric carbon atoms. They can thus exist in the form of enantiomers or of diastereoisomers. These enantiomers and diastereoisomers, and also their mixtures, including racemic mixtures, form part of the invention.

The compounds of formula (I) can also exist in the form of bases or of addition salts with acids. Such addition salts form part of the invention.

These salts can be prepared with pharmaceutically acceptable acids but the salts of other acids, of use, for example, in the purification or the isolation of the compounds of formula (I), also form part of the invention.

The compounds of formula (I) can also exist in the form of hydrates or of solvates, namely in the form of combinations or associations with one or more molecules of water or with a solvent. Such hydrates and solvates also form part of the invention.

In the context of the present invention:
$C_t$-$C_z$, where t and z can take the values from 1 to 7, is understood to mean a carbon chain which can have from t to z carbon atoms; for example, $C_1$-$C_3$ is understood to mean a carbon chain which can have from 1 to 3 carbon atoms;
a halogen atom is understood to mean a fluorine, chlorine, bromine or iodine atom;
an alkyl group is understood to mean a saturated, linear or branched, aliphatic group. Mention may be made, as examples, of the methyl, ethyl, propyl, isopropyl, butyl, isobutyl, tert-butyl or pentyl groups, and the like;
an alkoxy group is understood to mean an —O-alkyl radical, the alkyl group of which is as defined above;
an alkylene is understood to mean a saturated, linear or branched, divalent alkyl group; for example, a $C_{1-3}$-alkylene group represents a linear or branched divalent carbon chain of 1 to 3 carbon atoms, for example a methylene, ethylene, 1-methylethylene or propylene;
a cycloalkyl is understood to mean a cyclic carbon group. Mention may be made, as examples, of the cyclopropyl, cyclobutyl, cyclopentyl or cyclohexyl groups, and the like;
a fluoroalkyl is understood to mean an alkyl group, one or more hydrogen atoms of which have been substituted by a fluorine atom;
a fluoroalkoxy is understood to mean an alkoxy group, one or more hydrogen atoms of which have been substituted by a fluorine atom;
a heterocycloalkyl group is understood to mean a 3- to 7-membered cyclic group comprising 1 or 2 heteroatoms chosen from O, S or N; mention may be made, as examples of heterocycloalkyl groups, of the pyrrolidinyl, piperazinyl or morpholinyl groups;
an aryl group is understood to mean an aromatic cyclic group comprising between 6 and 10 carbon atoms. Mention may be made, as examples of aryl groups, of the phenyl or naphthyl groups;
a heteroaryl group is understood to mean a partially saturated or aromatic 5- to 15-membered cyclic group comprising from 1 to 4 heteroatoms chosen from O, S or N. Mention may be made, as examples, of the indolyl, furyl, pyrrolyl, thiazolyl, pyrazolyl, pyridinyl, pyrimidinyl, benzodioxolyl, benzofuryl, benzothienyl, benzoxadiazolyl, benzotriazolyl, quinolinyl, isoquinolinyl, dibenzofuryl, dibenzothienyl, imidazolyl, triazolyl, tetrazolyl, oxazolyl, oxadiazolyl, thiadiazolyl, thienyl, isoxazolyl or isothiazolyl groups.

Among the compounds of formula (I) which are subject-matters of the invention, a first subgroup of compounds is composed of the compounds for which:

R represents
either a hydrogen or halogen atom;
or a hydroxyl group;
or a heterocycloalkyl, aryl or heteroaryl group; it being possible for this group optionally to be substituted by one or more groups chosen from halogen atoms or ($C_1$-$C_6$)alkyl, ($C_1$-$C_6$)alkoxy, ($C_1$-$C_6$)fluoroalkyl, ($C_1$-$C_6$)fluoroalkoxy, nitro, cyano, hydroxyl, amino, ($C_1$-$C_6$)alkylamino or di($C_1$-$C_6$)alkylamino, heterocycloalkyl, aryl, aryl-($C_1$-$C_6$)alkylene, heteroaryl, aryl-O— or —C(O)—($C_1$-$C_6$)alkyl groups, the heterocycloalkyl group optionally being substituted by —C(O)O($CH_3$)$_3$;
n represents 1 or 2;
m represents 1 or 2;
o represents 1 or 2.

Among the compounds of formula (I) which are subject-matters of the invention, a second subgroup of compounds is composed of the compounds for which:
R represents
either a halogen atom, more particularly a chlorine;
or a hydroxyl group;
or a heterocycloalkyl group, more particularly a pyrrolidinyl or piperazinyl group, or an aryl group, more particularly a phenyl or naphthyl group, or a heteroaryl group, more particularly a pyrazolyl, indolyl, pyridinyl, benzofuryl, quinolinyl, benzothienyl, furyl, dibenzofuryl, pyrrolyl, pyrimidinyl, benzotriazolyl, dibenzothienyl, benzoxadiazolyl, thiazolyl or isoquinolinyl group; it being possible for this group optionally to be substituted by one or more groups, more particularly by one or two groups, chosen from halogen atoms, more particularly fluorine, or ($C_1$-$C_6$)alkyl, more particularly methyl, ($C_1$-$C_6$)alkoxy, more particularly methoxy, ($C_1$-$C_6$)fluoroalkyl, more particularly trifluoromethyl, ($C_1$-$C_6$)fluoroalkoxy, more particularly trifluoromethoxy, di($C_1$-$C_6$)alkylamino, more particularly dimethylamino, heterocycloalkyl, more particularly morpholinyl, pyrrolidinyl or piperazinyl, aryl, more particularly phenyl, aryl-($C_1$-$C_6$)alkylene, more particularly benzyl, heteroaryl, more particularly pyrazolyl, aryl-O—, more particularly phenoxy, or —C(O)—($C_1$-$C_6$)alkyl, more particularly —C(O)—$CH_3$, groups; the heterocycloalkyl group optionally being substituted by —C(O)O($CH_3$)$_3$;
n represents 1 or 2;
m represents 1 or 2;
o represents 1.

Among the compounds of formula (I) which are subject-matters of the invention and of the second subgroup above, a third subgroup of compounds is composed of the compounds for which: n and m and o=1.

Among the compounds of formula (I) which are subject-matters of the invention and of the second subgroup above, a fourth subgroup of compounds is composed of the compounds for which: n and m=2 and o=1.

Mention may in particular be made, among the compounds of formula (I) which are subject-matters of the invention, of the following compounds:

1. 4-[6-(1-methyl-1H-pyrazol-4-yl)pyridin-3-yl]-1-azabicyclo[2.2.1]heptane
2. 5-[6-(1-methyl-1H-pyrazol-4-yl)pyridin-3-yl]-1-azabicyclo[3.3.1]nonane
3. 5-[6-(3,4-dimethoxyphenyl)pyridin-3-yl]-1-azabicyclo[3.3.1]nonane
4. 5-(1-azabicyclo[3.3.1]non-5-yl)pyridin-2-ol
5. 5-(6-chloropyridin-3-yl)-1-azabicyclo[3.3.1]nonane
6. 5-[5-(1-azabicyclo[2.2.1]hept-4-yl)pyridin-2-yl]-1-methyl-1H-indole
7. 5-(1-azabicyclo[3.3.1]non-5-yl)-2,4'-bipyridine
8. 4-[6-(4-fluorophenyl)pyridin-3-yl]-1-azabicylo[2.2.1]heptane
9. 4-[6-(1-benzofur-2-yl)pyridin-3-yl]-1-azabicyclo[2.2.1]heptane
10. 5-[6-(1-benzofur-2-yl)pyridin-3-yl]-1-azabicyclo[3.3.1]nonane
11. 5-(1-azabicyclo[2.2.1]hept-4-yl)-2,4'-bipyridine
12. 6-[5-(1-azabicyclo[2.2.1]hept-4-yl)pyridin-2-yl]quinoline
13. 4-[6-(4-benzylpiperazin-1-yl)pyridin-3-yl]-1-azabicyclo[2.2.1]heptane
14. 4-[6-(1-benzothien-2-yl)pyridin-3-yl]-1-azabicyclo[2.2.1]heptane
15. 5-(1-azabicyclo[2.2.1]hept-4-yl)pyridin-2-ol
16. 4-[6-(1,3-benzodioxol-5-yl)pyridin-3-yl]-1-azabicyclo[2.2.1]heptane
17. 4-[6-(3,4-dimethoxyphenyl)pyridin-3-yl]-1-azabicyclo[2.2.1]heptane
18. 4-{6-[3-(trifluoromethyl)phenyl]pyridin-3-yl}-1-azabicyclo[2.2.1]heptane
19. 4-[6-(3-fluorophenyl)pyridin-3-yl]-1-azabicyclo[2.2.1]heptane
20. 5-[6-(3-fluorophenyl)pyridin-3-yl]-1-azabicyclo[3.3.1]nonane
21. 4-[6-(3-furyl)pyridin-3-yl]-1-azabicyclo[2.2.1]heptane
22. 4-(6-(dibenzo[b,d]fur-4-yl)pyridin-3-yl)-1-azabicyclo[2.2.1]heptane
23. 3-[5-(1-azabicyclo[2.2.1]hept-4-yl)pyridin-2-yl]quinoline
24. 5-(1-azabicyclo[2.2.1]hept-4-yl)-2,3'-bipyridine
25. 4-{6-[4-(trifluoromethoxy)phenyl]pyridin-3-yl}-1-azabicyclo[2.2.1]heptane
26. 5-[6-(1-benzothien-2-yl)pyridin-3-yl]-1-azabicyclo[3.3.1]nonane
27. 4-[6-(4-fluoro-2-methoxyphenyl)pyridin-3-yl]-1-azabicyclo[2.2.1]heptane
28. 4-[6-(1H-pyrrol-3-yl)pyridin-3-yl]-1-azabicyclo[2.2.1]heptane
29. 4-(6-(pyrrolidin-1-yl)pyridin-3-yl)-1-azabicyclo[2.2.1]heptane
30. 5-(6-(dibenzo[b,d]fur-4-yl)pyridin-3-yl)-1-azabicyclo[3.3.1]nonane
31. 5-[6-(1,3-benzodioxol-5-yl)pyridin-3-yl]-1-azabicyclo[3.3.1]nonane
32. 6-[5-(1-azabicyclo[3.3.1]non-5-yl)pyridin-2-yl]quinoline
33. 5-[5-(1-azabicyclo[3.3.1]non-5-yl)pyridin-2-yl]-1-methyl-1H-indole
34. 5-[6-(1H-pyrrol-3-yl)pyridin-3-yl]-1-azabicyclo[3.3.1]nonane
35. 5-{6-[3-(trifluoromethyl)phenyl]pyridin-3-yl}-1-azabicyclo[3.3.1]nonane
36. 5-[6-(4-fluorophenyl)pyridin-3-yl]-1-azabicyclo[3.3.1]nonane
37. 4-(6-(pyrimidin-5-yl)pyridin-3-yl)-1-azabicyclo[2.2.1]heptane
38. 4-[6-(2,4-dimethoxypyrimidin-5-yl)pyridin-3-yl]-1-azabicyclo[2.2.1]heptane
39. 5-(6-(biphenyl-4-yl)pyridin-3-yl)-1-azabicyclo[3.3.1]nonane
40. 5-[6-(3-furyl)pyridin-3-yl]-1-azabicyclo[3.3.1]nonane
41. 5-(1-azabicyclo[3.3.1]non-5-yl)-2,3'-bipyridine
42. 5-{6-[4-(trifluoromethoxy)phenyl]pyridin-3-yl}-1-azabicyclo[3.3.1]nonane
43. 5-[6-(4-fluoro-2-methoxyphenyl)pyridin-3-yl]-1-azabicyclo[3.3.1]nonane 44. 3-[5-(1-azabicyclo[3.3.1]non-5-yl)pyridin-2-yl]quinoline
45. 4-(6-(biphenyl-4-yl)pyridin-3-yl)-1-azabicyclo[2.2.1]heptane
46. 8-[5-(1-azabicyclo[2.2.1]hept-4-yl)pyridin-2-yl]quinoline
47. 1-[5-(1-azabicyclo[3.3.1]non-5-yl)pyridin-2-yl]-1H-1,2,3-benzotriazole
48. 5-(6-(dibenzo[b,d]thien-2-yl)pyridin-3-yl)-1-azabicyclo[3.3.1]nonane
49. 5-[6-(4-methoxyphenyl)pyridin-3-yl]-1-azabicyclo[3.3.1]nonane
50. 5-[6-(3-methoxyphenyl)pyridin-3-yl]-1-azabicyclo[3.3.1]nonane
51. 5-[5-(1-azabicyclo[2.2.1]hept-4-yl)pyridin-2-yl]-2,1,3-benzoxadiazole
52. 4-[6-(2-(morpholin-4-yl)pyrimidin-5-yl)pyridin-3-yl]-1-azabicyclo[2.2.1]heptane
53. 4-[6-(1-methyl-1H-pyrrol-2-yl)pyridin-3-yl]-1-azabicyclo[2.2.1]heptane
54. 4-[6-(3-fluoro-5-methoxyphenyl)pyridin-3-yl]-1-azabicyclo[2.2.1]heptane
55. 4-[6-(3-fluoro-4-methoxyphenyl)pyridin-3-yl]-1-azabicyclo[2.2.1]heptane
56. 4-[6-(2-fluoro-3-methoxyphenyl)pyridin-3-yl]-1-azabicyclo[2.2.1]heptane
57. 5-[6-(3-fluoro-4-methoxyphenyl)pyridin-3-yl]-1-azabicyclo[3.3.1]nonane
58. 5-[6-(2-fluoro-3-methoxyphenyl)pyridin-3-yl]-1-azabicyclo[3.3.1]nonane
59. 5-[6-(1-methyl-1H-pyrrol-2-yl)pyridin-3-yl]-1-azabicyclo[3.3.1]nonane
60. 5-[6-2-furyl)pyridin-3-yl]-1-azabicyclo[3.3.1]nonane
61. 5-{6-[3-(1H-pyrazol-1-yl)phenyl]pyridin-3-yl}-1-azabicyclo[3.3.1]nonane
62. 4-[6-(thiazol-2-yl)pyridin-3-yl]-1-azabicyclo[2.2.1]heptane
63. 5-(6-(pyrimidin-5-yl)pyridin-3-yl)-1-azabicyclo[3.3.1]nonane
64. 5-[6-(1-naphthyl)pyridin-3-yl]-1-azabicyclo[3.3.1]nonane
65. 5-[6-(2-(morpholin-4-yl)pyrimidin-5-yl)pyridin-3-yl]-1-azabicyclo[3.3.1]nonane
66. 5-[6-(2,4-dimethoxypyrimidin-5-yl)pyridin-3-yl]-1-azabicyclo[3.3.1]nonane
67. 5-[5-(1-azabicyclo[3.3.1]non-5-yl)pyridin-2-yl]-2,1,3-benzoxadiazole
68. 5-(6-phenylpyridin-3-yl)-1-azabicyclo[3.3.1]nonane
69. 5-[6-(2,5-dimethoxyphenyl)pyridin-3-yl]-1-azabicyclo[3.3.1]nonane
70. 5-{6-[4-(trifluoromethyl)phenyl]pyridin-3-yl}-1-azabicyclo[3.3.1]nonane
71. 5-(1-azabicyclo[3.3.1]non-5-yl)-4'-methoxy-2,3'-bipyridine
72. 4-[5-(1-azabicyclo[3.3.1]non-5-yl)pyridin-2-yl]isoquinoline
73. 5-{6-[3,5-bis(trifluoromethyl)phenyl]pyridin-3-yl}-1-azabicyclo[3.3.1]nonane
74. 5-[6-(thiazol-2-yl)pyridin-3-yl]-1-azabicyclo[3.3.1]nonane
75. 5-[6-(4-phenoxyphenyl)pyridin-3-yl]-1-azabicyclo[3.3.1]nonane
76. 5-[6-(2-fluorophenyl)pyridin-3-yl]-1-azabicyclo[3.3.1]nonane
77. 5-(1-azabicyclo[3.3.1]non-5-yl)-6'-(pyrrolidin-1-yl)-2,3'-bipyridine
78. tert-butyl 4-[5-(1-azabicyclo[3.3.1]non-5-yl)-2,3'-bipyridin-6'-yl]piperazine-1-carboxylate
79. 5-[6-(2-methoxyphenyl)pyridin-3-yl]-1-azabicyclo[3.3.1]nonane
80. 5-[6-(2,4-dimethoxyphenyl)pyridin-3-yl]-1-azabicyclo[3.3.1]nonane
81. 5-{6-[3-(trifluoromethoxy)phenyl]pyridin-3-yl}-1-azabicyclo[3.3.1]nonane
82. 3-[5-(1-azabicyclo[3.3.1]non-5-yl)pyridin-2-yl]-N,N-dimethylaminophenyl
83. 4-[5-(1-azabicyclo[2.2.1]hept-4-yl)pyridin-2-yl]isoquinoline
84. 5-[5-(1-azabicyclo[2.2.1]hept-4-yl)pyridin-2-yl]isoquinoline
85. 4-(6-phenylpyridin-3-yl)-1-azabicyclo[2.2.1]heptane
86. 4-{6-[3,5-bis(trifluoromethyl)phenyl]pyridin-3-yl}-1-azabicyclo[2.2.1]heptane
87. 5-(1-azabicyclo[2.2.1]hept-4-yl)-4'-methoxy-2,3'-bipyridine
88. tert-butyl 4-[5-(1-azabicyclo[2.2.1]hept-4-yl)-2,3'-bipyridin-6'-yl]piperazine-1-carboxylate
89. 5-[5-(1-azabicyclo[3.3.1]non-5-yl)pyridin-2-yl]isoquinoline
90. 5-(1-azabicyclo[2.2.1]hept-4-yl)-6'-fluoro-2,3'-bipyridine
91. 5-(1-azabicyclo[3.3.1]non-5-yl)-2'-fluoro-2,3'-bipyridine
92. 4-[6-(2-methoxyphenyl)pyridin-3-yl]-1-azabicyclo[2.2.1]heptane
93. 4-[6-(2,4-dimethoxyphenyl)pyridin-3-yl]-1-azabicyclo[2.2.1]heptane
94. 4-[6-(2,5-dimethoxyphenyl)pyridin-3-yl]-1-azabicyclo[2.2.1]heptane
95. 4-[6-(2-fluorophenyl)pyridin-3-yl]-1-azabicyclo[2.2.1]heptane
96. 4-[6-(4-methoxyphenyl)pyridin-3-yl]-1-azabicyclo[2.2.1]heptane
97. 4-[6-(2-naphthyl)pyridin-3-yl]-1-azabicyclo[2.2.1]heptane
98. 4-[6-(4-phenoxyphenyl)pyridin-3-yl]-1-azabicyclo[2.2.1]heptane
99. 4-{6-[2-(trifluoromethyl)phenyl]pyridin-3-yl}-1-azabicyclo[2.2.1]heptane
100. 5-[6-(2-naphthyl)pyridin-3-yl]-1-azabicyclo[3.3.1]nonane
101. 5-(1-azabicyclo[2.2.1]hept-4-yl)-2'-fluoro-2,3'-bipyridine
102. 5-(1-azabicyclo[3.3.1]non-5-yl)-6'-fluoro-2,3'-bipyridine
103. 4-[6-(3-(trifluoromethoxy)phenyl)pyridin-3-yl]-1-azabicyclo[2.2.1]heptane
104. 5-[5-(1-azabicyclo[3.3.1]non-5-yl)pyridin-2-yl]quinoline
105. 5-[6-(2-fluorobiphenyl-4-yl)pyridin-3-yl]-1-azabicyclo[3.3.1]nonane
106. 1-{3-[5-(1-azabicyclo[3.3.1]non-5-yl)pyridin-2-yl]phenyl}ethanone
107. 1-{3-[5-(1-azabicyclo[2.2.1]hept-4-yl)pyridin-2-yl]phenyl}ethanone
108. 4-(6-(4-methylphenyl)pyridin-3-yl)-1-azabicyclo[2.2.1]heptane
109. 4-[6-(2-fluorobiphenyl-4-yl)pyridin-3-yl]-1-azabicyclo[2.2.1]heptane
110. 5-[5-(1-azabicyclo[2.2.1]hept-4-yl)pyridin-2-yl]quinoline
111. 4-[6-(3-methoxyphenyl)pyridin-3-yl]-1-azabicyclo[2.2.1]heptane 112. 4-[6-(3,4-difluorophenyl)pyridin-3-yl]-1-azabicyclo[2.2.1]heptane
113. 4-[6-(3-(pyrazol-1-yl)phenyl)pyridin-3-yl]-1-azabicyclo[2.2.1]heptane In that which follows, the term "protective group" is understood to mean a group which makes it possible, on the one hand, to protect a reactive functional group, such as a hydroxyl or an amine, during a synthesis and, on the other hand, to regenerate the reactive functional group intact at the end of the synthesis. Examples of protective groups and also of methods for protection and deprotection are given in "Protective Groups in Organic Synthesis", Green et al., $2^{nd}$ Edition (John Wiley & Sons, Inc., New York), 1991.

The term "leaving group" is understood to mean, in that which follows, a group which can be easily cleaved from a molecule by splitting a heterolytic bond with departure of an electron pair. This group can thus be easily replaced by another group during the substitution reaction, for example. Such leaving groups are, for example, halogens or an activated hydroxyl group, such as a methanesulfonate, benzenesulfonate, p-toluenesulfonate, triflate, acetate, and the like. Examples of leaving groups and references for their preparation are given in "Advances in Organic Chemistry", J. March, $3^{rd}$ Edition, Wiley Interscience, 1985, pp. 310-316.

In accordance with the invention and in the case where n and m and o=1, the compounds of general formula (I) can be prepared by the process illustrated by the following scheme 1.

The compound of formula (II) is reacted with the alkyl bromoacetate of general formula (III) in which $R_1$ represents a ($C_1$-$C_4$)alkyl group in the presence of a base, such as lithium diisopropylamide, in order to obtain a compound of general formula (IV). The hydrogenation of the nitrile functional group under a hydrogen atmosphere of between 1 and 6 atmospheres in the presence of a catalyst, such as, for example, Raney nickel, provides a compound of general formula (V). The compound of general formula (V) is reduced by a reducing agent, such as, for example, lithium aluminum hydride, to result in the compound of formula (VI). The compound of formula (VI) is converted to a compound of formula (VII), for example in the presence of concentrated hydrobromic acid. The compound of formula (VII) is reacted in a basic medium with a base, such as sodium carbonate, in order to obtain a compound of formula (VIII). The treatment of this compound, for example with phosphorus oxychloride, results in the compound of formula (IX). The compounds of general formula (I) can subsequently be prepared from the compound of formula (IX) according to any method known to a person skilled in the art, such as, for example:

with boronic acid of formula R—B(OH)$_2$, in which R is as defined in the general formula (I), in the presence of a palladium catalyst, for example tetrakis(triphenylphosphine)palladium;

with a compound of formula R—H, in which R is as defined in the general formula (I), in the presence or absence of a strong base, for example sodium hydride, in a solvent, for example dimethylformamide, or without solvent;

with a compound of formula R—H, in which R is as defined in the general formula (I), in the presence of a base, for example sodium tert-butoxide, of a palladium catalyst, for example palladium(II) acetate, and of a ligand, for example 2-dicyclohexylphosphino-2'-(N,N-dimethylamino)biphenyl;

with a stannous derivative of formula R—Sn[(CH$_2$)$_3$CH$_3$]$_3$, in which R is as defined in the general formula (I), in the presence of a palladium catalyst, for example bis(triphenylphosphino)dichloropalladium;

with a compound of formula R—H, in which R is as defined in the general formula (I), in the presence of n-butyllithium, of zinc chloride and of a palladium catalyst, for example tetrakis(triphenylphosphine)palladium.

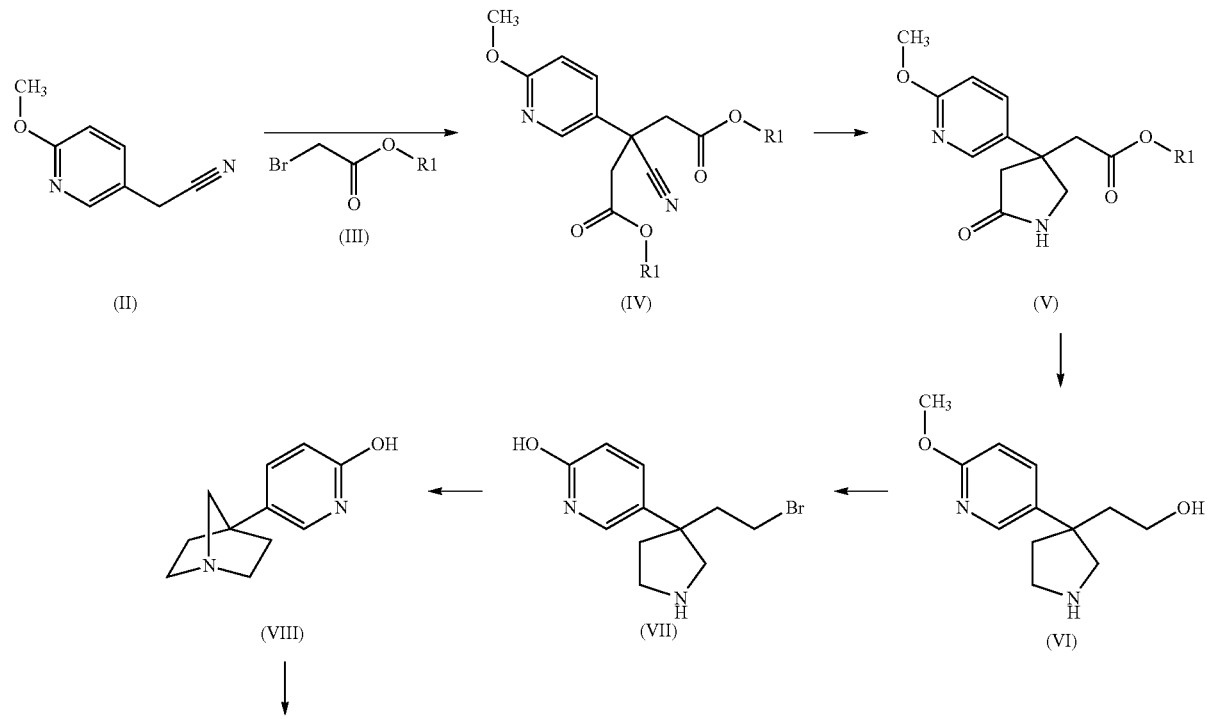

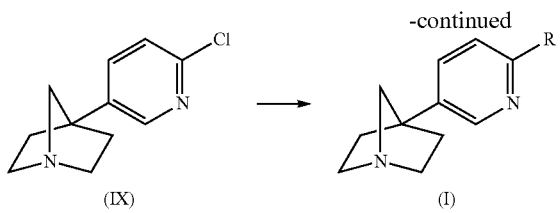

In accordance with the invention in the case where n and m=2 and o=1, the compounds of general formula (I) can be prepared by the process illustrated by the following scheme 2.

The compound of formula (II) is reacted with the alkyl acrylate of general formula (X), in which $R_1$ represents a $(C_1-C_4)$alkyl group, in the presence of a base, such as Triton B, in order to obtain a compound of general formula (XI). The compound of general formula (I) is subsequently obtained from the intermediates (XII) to (XVI) according to stages analogous to those which have made it possible to prepare the intermediates (V) to (IX) as described above in scheme 1.

available commercially or are described in the literature or else can be prepared according to methods which are described therein or which are known to a person skilled in the art.

The compounds of general formula (I) corresponding to the other values of n, m and o can be obtained by adaptation of the processes described in schemes 1 and 2 according to conventional synthetic methods of organic chemistry which can be adapted by a person skilled in the art.

Another subject-matter of the invention, according to another of its aspects, is the compounds of formulae (III) to

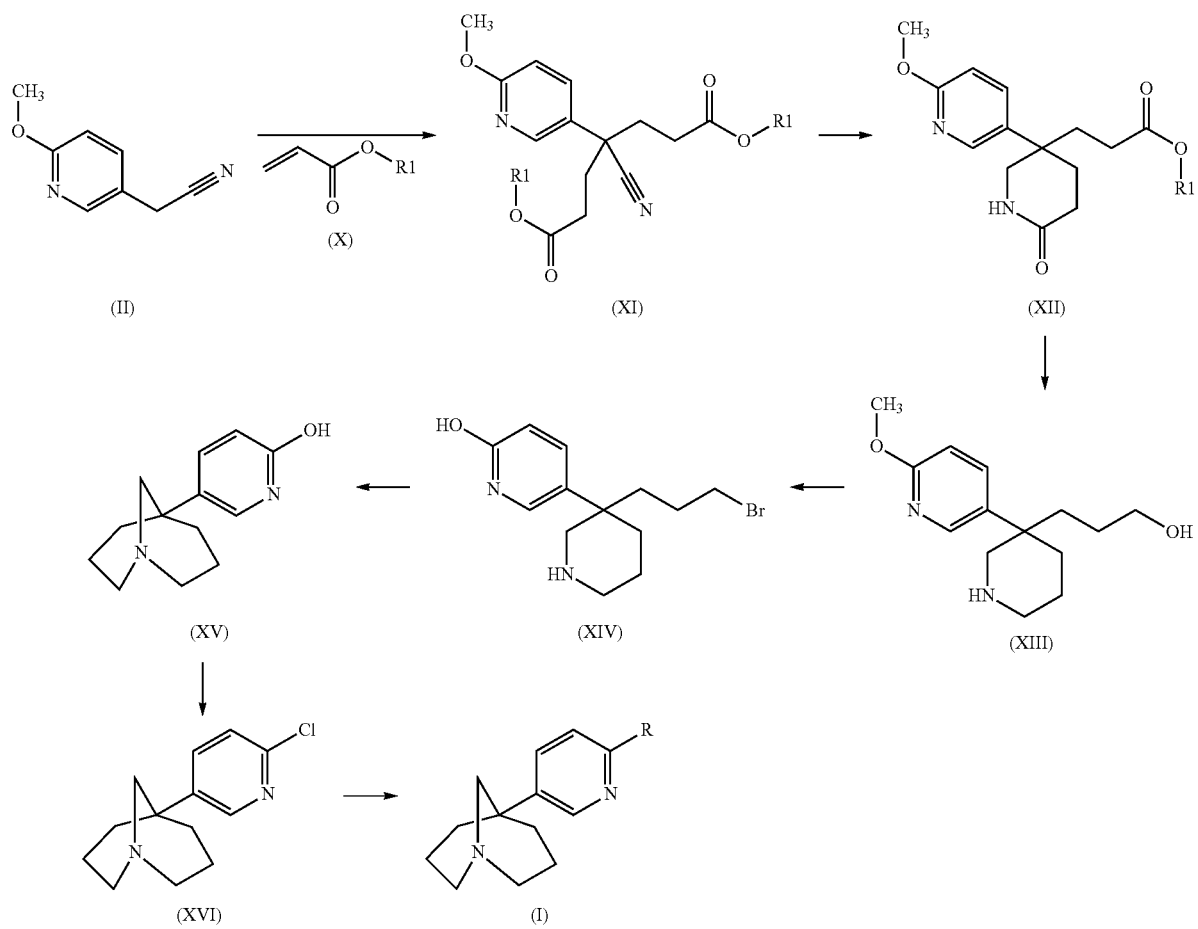

The compound of formula (II) is accessible by methods described in the literature, such as, for example, in the document WO2004/111031.

In schemes 1 and 2, the starting compounds and the reactants, when their method of preparation is not described, are (XVI). These compounds are of use as intermediates in the synthesis of the compounds of general formula (I). In particular, a subject-matter of the invention is the intermediate (XVI). The following examples describe the preparation of some compounds in accordance with the invention. These examples are not limiting and serve only to illustrate the present invention. The numbers of the compounds given in brackets in the titles refer to those given in the first column of the following table, in which the chemical structures and the physical properties of some compounds according to the invention are illustrated.

EXAMPLE 1

Compound No. 4

5-(1-Azabicyclo[3.3.1]non-5-yl)pyridin-2-ol

1.1 Diethyl 4-cyano-4-(6-methoxypyridin-3-yl)heptanedioate 2.775 g (18.73 mmol) of (6-methoxypyridin-3-yl)acetonitrile (WO2004/111031) are introduced into 125 ml of anhydrous acetonitrile in a 250 ml round-bottomed flask under an argon atmosphere. 0.87 ml (1.87 mmol) of Triton B (40% in methanol) is added, the reaction mixture is brought to reflux and 20.40 ml (187.30 mmol) of ethyl acrylate are added dropwise. The reaction medium is subsequently stirred at reflux for 48 hours, cooled to ambient temperature and concentrated under reduced pressure. The residue thus obtained is poured into a saturated aqueous ammonium chloride solution and extracted twice with dichloromethane. The organic phases are combined, dried over sodium sulfate, filtered and concentrated under reduced pressure. The residue obtained is purified by chromatography on a column of silica gel, elution being carried out with a mixture of chloroform, methanol and aqueous ammonia in the proportions 90/10/1.

7.981 g of product are obtained in the form of an orange oil.
$^1$H NMR (CDCl$_3$, 200 MHz): δ (ppm): 8.18 (d, 1H), 7.45 (dd, 1H), 6.71 (d, 1H), 4.00 (q, 4H), 3.87 (s, 3H), 2.55-1.97 (m, 8H), 1.14 (t, 6H).

1.2 Ethyl 3-[3-(6-methoxypyridin-3-yl)-6-oxopiperidin-3-yl]propanoate 1.999 g (5.74 mmol) of diethyl 4-cyano-4-(6-methoxypyridin-3-yl)heptanedioate as obtained in stage 1.1, in solution in 115 ml of ethyl alcohol, are introduced into a hydrogenation flask in the presence of Raney nickel (0.1 eq.), 50% in water. The medium is stirred under approximately 5 atmospheres of hydrogen at 60° C. for 6 h and then filtered through diatomaceous earth, and the solvent is removed by evaporation under reduced pressure. The residue obtained is purified by chromatography on a column of silica gel, elution being carried out with a mixture of chloroform, methanol and aqueous ammonia in the proportions 90/10/1, to provide 1.231 g of the desired compound in the form of a yellow wax.
$^1$H NMR (CDCl$_3$, 200 MHz): δ (ppm): 8.13 (d, 1H), 7.55 (dd, 1H), 6.80 (d, 1H), 6.45 (br s, 1H), 4.09 (q, 2H), 3.96 (s, 3H), 3.80-3.37 (AB, 2H), 2.52-1.88 (m, 8H), 1.21 (t, 3H).

1.3 3-[3-(6-Methoxypyridin-3-yl)piperidin-3-yl]propan-1-ol 2.321 g (7.58 mmol) of ethyl 3-[3-(6-methoxypyridin-3-yl)-6-oxopiperidin-3-yl]propanoate obtained in stage 1.2, in solution in 128 ml of anhydrous tetrahydrofuran, are introduced at ambient temperature into a 250 ml round-bottomed flask. 2.876 g (75.8 mmol) of lithium aluminum hydride are added portionwise and the resulting mixture is subsequently stirred at ambient temperature for 3 hours. The mixture is subsequently hydrolyzed with a saturated aqueous sodium sulfate solution, filtered through celite and concentrated under reduced pressure. The residue obtained is purified by chromatography on a column of silica gel, elution being carried out with a mixture of chloroform, methanol and aqueous ammonia in the proportions 90/10/1, to provide 1.80 g of the desired compound in the form of a yellow wax.
$^1$H NMR (CDCl$_3$, 200 MHz): δ (ppm): 7.94 (d, 1H), 7.37 (dd, 1H), 6.57 (d, 1H), 3.78 (s, 3H), 3.31 (t, 2H), 3.12-2.70 (AB, 2H), 2.65 (t, 2H), 2.11 (br s, 2H), 2.01-0.97 (m, 8H).

1.4 5-[3-(3-Bromopropyl)piperidin-3-yl]pyridin-2-ol hydrobromide (1:1)

0.100 g (0.4 mmol) of 3-[3-(6-methoxypyridin-3-yl)piperidin-3-yl]propan-1-ol obtained in stage 1.3, in solution in 5 ml of aqueous hydrobromic acid (48% by weight solution), is introduced into a sealed tube. The reaction medium is stirred at 110° C. for 12 hours. This solution is then brought back to ambient temperature and concentrated under reduced pressure. The resulting residue is dissolved in methanol and evaporated twice under reduced pressure, and triturated from diethyl ether, to result, after filtration, in 0.150 g of the desired compound in the form of a brown powder.

Melting point: 230° C.
$^1$H NMR (D$_2$O, 200 MHz): δ (ppm): 7.88 (dd, 1H), 7.51 (d, 1H), 6.80 (d, 1H), 3.65-3.27 (AB, 2H), 3.31 (t, 2H), 3.24-2.90 (m, 2H), 2.32-1.25 (m, 8H).

1.5 5-(1-Azabicyclo[3.3.1]non-5-yl)pyridin-2-ol (Compound No. 4)

2.17 g (5.71 mmol) of 5-[3-(3-bromopropyl)piperidin-3-yl]pyridin-2-ol hydrobromide (1:1) obtained in stage 1.4, in solution in 114 ml of chloroform and 40 ml of water, are introduced into a 250 ml round-bottomed flask. 3.94 g (28.54 mmol) of sodium carbonate are added and the reaction mixture is stirred at 80° C. for 2 hours. The reaction mixture is subsequently brought back to ambient temperature, poured into a separating funnel and extracted twice with chloroform. The organic phases are combined, dried over sodium sulfate, filtered and concentrated under reduced pressure. The residue thus obtained is triturated from diethyl ether to result, after filtration and drying, in 0.813 g of the desired compound in the form of a white powder.

Melting point: 191-192° C.
$^1$H NMR (d$_6$-DMSO, 200 MHz): δ (ppm): 7.89 (dd, 1H), 7.41 (d, 1H), 6.65 (d, 1H), 3.70-3.34 (m, 6H), 2.70-1.83 (m, 8H).

EXAMPLE 2

Compound No. 5

5-(6-Chloropyridin-3-yl)-1-azabicyclo[3.3.1]nonane 1 g (4.59 mmol) of 5-(1-azabicyclo[3.3.1]non-5-yl)pyridin-2-ol obtained in Example 1, in solution in 12.8 mol (137.7 mmol) of phosphorus oxychloride, is introduced into a sealed tube and the combined mixture is subsequently stirred at 140° C. for 45 minutes. The reaction mixture is subsequently brought back to ambient temperature, poured onto 200 g of crushed ice and stirred for 15 minutes. The medium is then very slowly adjusted to pH 10 with a concentrated sodium hydroxide solution. The combined mixture is subsequently extracted twice with chloroform and the organic phases are subsequently combined, dried over sodium sulfate, filtered and concentrated under reduced pressure to provide 461 mg of the desired compound in the form of a brown powder.

Melting point: 245-246° C.

$^1$H NMR (CDCl$_3$, 200 MHz): δ (ppm): 8.29 (d, 1H), 7.55 (dd, 1H), 7.23 (d, 1H), 3.30-3.10 (m, 6H), 2.42-2.00 (m, 4H), 1.92-1.63 (m, 4H).

EXAMPLE 3

Compound No. 3

5-[6-(3,4-Dimethoxyphenyl)pyridin-3-yl]-1-azabicyclo[3.3.1]nonane hydrochloride (2:1)

0.055 g (0.23 mmol) of 5-(6-chloropyridin-3-yl)-1-azabicyclo[3.3.1]nonane obtained in Example 2, in solution in 12 ml of a 1,2-dimethoxyethane/water 8/4 mixture, is introduced into a 100 ml round-bottomed flask. 0.106 g (0.58 mmol) of 3,4-dimethoxyphenylboronic acid, 0.08 g (0.58 mmol) of potassium carbonate and 0.024 g (0.03 mmol) of dichlorobis(triphenylphosphine)palladium(II) are then successively introduced under an argon atmosphere. The mixture is heated at 110° C. for 2 hours, cooled to ambient temperature and poured into 300 ml of a saturated aqueous sodium carbonate solution. The aqueous phase is extracted twice with 100 ml of chloroform, and the combined organic phases are dried over sodium sulfate and concentrated under reduced pressure. The residue is purified by chromatography on a column of silica gel, elution being carried out with a mixture of chloroform, methanol and aqueous ammonia in the proportions 90/10/1. The compound obtained in the base form (5-[6-(3,4-dimethoxyphenyl)pyridin-3-yl]-1-azabicyclo[3.3.1]nonane) is converted to the hydrochloride by adding two equivalents of hydrochloric acid in solution (5-6 N) in isopropyl alcohol. After triturating from diethyl ether, 0.035 g of the expected product is obtained in the form of a yellow powder.

Melting point: 235-236° C.

$^1$H NMR (d$_6$-DMSO): δ (ppm): 8.57 (s, 1H), 7.84-7.50 (m, 4H), 7.01 (d; 1H), 3.82 (s, 3H), 3.77 (s, 3H), 3.30 (br s, 2H), 3.13-2.83 (m, 4H), 2.31-1.95 (m, 4H), 1.88-1.61 (m, 2H), 1.55-1.33 (m, H).

EXAMPLE 4

Compound No. 15

5-(1-Azabicyclo[2.2.1]hept-4-yl]pyridin-2-ol 4.1 Diethyl 3-cyano-3-(6-methoxypyridin-3-yl)pentanedioate 10.12 ml (20.25 mmol) of lithium diisopropylamide are introduced in 22 ml of anhydrous tetrahydrofuran in a 100 ml three-necked round-bottomed flask under an argon atmosphere at −78° C. 1.00 g (6.75 mmol) of (6-methoxypyridin-3-yl)acetonitrile (WO2004/111031) in solution of 5 ml of anhydrous tetrahydrofuran is added. The reaction mixture is subsequently brought back gently to 0° C. and stirred at this temperature for one hour. The reaction medium is then cooled to −78° C. and 2.25 ml (20.25 mmol) of ethyl bromoacetate are added dropwise. The resulting mixture is subsequently brought back slowly to ambient temperature and then left stirring for 12 hours. The reaction medium is subsequently poured into a saturated aqueous ammonium chloride solution and extracted twice with diethyl ether. The organic phases are combined, dried over sodium sulfate, filtered and concentrated under reduced pressure. The residue obtained is purified by chromatography on a column of silica gel, elution being carried out with a mixture of cyclohexane and ethyl acetate in the proportions of 90/10.

1.758 g of product are obtained in the form of a brown oil.

$^1$H NMR (CDCl$_3$, 200 MHz): δ (ppm): 8.08 (d, 1H), 7.49 (dd, 1H), 6.55 (d, 1H), 3.90 (q, 4H), 3.72 (s, 3H), 3.11-2.79 (AB, 4H) 0.97 (t, 6H).

4.2 Ethyl[3-(6-methoxypyridin-3-yl)-5-oxopyrrolidin-3-yl]acetate 2.990 g (9.33 mmol) of diethyl 3-cyano-3-(6-methoxypyridin-3-yl)pentanedioate as obtained in stage 4.1, in solution in 186 ml of ethyl alcohol, are introduced into a hydrogenation flask in the presence of Raney nickel (0.1 eq.), 50% in water. The medium is stirred under approximately 5 atmospheres of hydrogen at 60° C. for 6 h and then filtered through diatomaceous earth, and the solvent is removed by evaporating under reduced pressure. The residue obtained is purified by chromatography on a column of silica gel, elution being carried out with a mixture of chloroform, methanol and aqueous ammonia in the proportions 90/10/1, to provide 1.5 g of the desired compound in the form of a yellow wax.

$^1$H NMR (CDCl$_3$, 200 MHz): δ (ppm): 7.93 (d, 1H), 7.37 (dd, 1H), 6.66 (d, 1H), 6.52 (br s, 1H), 3.91 (q, 2H), 3.85 (s, 3H), 3.84-3.57 (AB, 2H), 2.71 (t, 4H), 1.04 (t, 3H).

4.3 2-[3-(6-Methoxypyridin-3-yl)pyrrolidin-3-yl] ethanol 1.50 g (5.39 mmol) of ethyl[3-(6-methoxypyridin-3-yl)-5-oxopyrrolidin-3-yl]acetate obtained in stage 4.2, in solution in 90 ml of anhydrous tetrahydrofuran, are introduced into a 250 ml round-bottomed flask at ambient temperature. 2.046 g (53.90 mmol) of lithium aluminum hydride are added portionwise and the resulting mixture is subsequently stirred at ambient temperature for 3 hours. The mixture is subsequently hydrolyzed with a saturated aqueous sodium sulfate solution, filtered through celite and concentrated under reduced pressure. The residue obtained is purified by chromatography on a column of silica gel, elution being carried out with a mixture of chloroform, methanol and aqueous ammonia in the proportions 90/10/1, to provide 0.41 g of the desired compound in the form of a yellow wax.

$^1$H NMR (CDCl$_3$, 200 MHz): δ (ppm): 7.95 (d, 1H), 7.39 (dd, 1H), 6.64 (d, 1H), 3.83 (s, 3H), 3.60-2.91 (m, 8H), 2.09 (t, 2H), 1.92-1.64 (m, 2H).

4.4 5-[3-(2-Bromoethyl)pyrrolidin-3-yl]pyridin-2-ol hydrobromide (1:1)

0.32 g (1.44 mmol) of 2-[3-(6-methoxypyridin-3-yl)pyrrolidin-3-yl]ethanol obtained in stage 4.3, in solution in 7.2 ml of aqueous hydrobromic acid (48% by weight solution), is introduced into a sealed tube. The reaction medium is stirred at 160° C. for 5 hours. This solution is then brought back to ambient temperature and concentrated under reduced pressure. The resulting residue is dissolved in methanol, evaporated twice under reduced pressure and triturated from diethyl ether, to result, after filtration in 0.5 g of the desired compound in the form of a brown gum.

$^1$H NMR (D$_2$O, 200 MHz): δ (ppm): 7.72 (dd, 1H), 7.49 (d, 1H), 6.65 (d, 1H), 3.78-2.90 (m, 6H), 2.55-2.05 (m, 4H).

4.5 5-(1-Azabicyclo[2.2.1]hept-4-yl)pyridine-2-ol (Compound No. 15)

1.5 g (4.26 mmol) of 5-[3-(2-bromoethyl)pyrrolidin-3-yl]pyridin-2-ol hydrobromide (1:1) obtained in stage 4.4, in solution in 85 ml of chloroform in 10 ml of water, are introduced into a 250 ml round-bottomed flask. 2.944 g (21.3 mmol) of sodium carbonate are added and the reaction mixture is stirred at 60° C. for 3 hours. The reaction mixture is subsequently brought back to ambient temperature, poured into a separating funnel and extracted twice with chloroform. The organic phases are combined, dried over sodium sulfate, filtered and concentrated under reduced pressure. The residue thus obtained is triturated from diethyl ether to result, after filtration and drying, in 0.265 g of the desired compound in the form of a brown powder.

Melting point: 170-172° C.

$^1$H NMR ($d_6$-DMSO, 200 MHz): δ (ppm): 7.48 (dd, 1H), 7.08 (d, 1H), 6.27 (d, 1H), 2.94-2.74 (m, 2H), 2.65-2.42 (m, 2H), 2.35 (s, 2H), 1.75-1.50 (m, 2H), 1.50-1.33 (m, 2H).

EXAMPLE 5

Compound No. 1

4-[6-(1-Methyl-1H-pyrazol-4-yl)pyridin-3-yl]-1-azabicyclo[2.2.1]heptane hydrochloride (2:1)

5.1 4-(6-Chloropyridin-3-yl)-1-azabicyclo[2.2.1]heptane 0.37 g (1.94 mmol) of 5-(1-azabicyclo[2.2.1]hept-4-yl)pyridin-2-ol obtained in Example 4, in solution in 5.44 ml (58.35 mmol) of phosphorus oxychloride, is introduced into a sealed tube and the combined mixture is subsequently stirred at 140° C. for 45 minutes. The reaction mixture is subsequently brought back to ambient temperature, poured onto 200 g of crushed ice and stirred for 15 minutes. The medium is then very slowly adjusted to pH 10 with a concentrated sodium hydroxide solution. The combined mixture is subsequently extracted twice with chloroform and the organic phases are subsequently combined, dried over sodium sulfate, filtered and concentrated under reduced pressure to provide 370 mg of the desired compound in the form of a brown powder.

Melting point: 70-72° C.

$^1$H NMR ($d_6$-DMSO, 200 MHz): δ (ppm): 8.36 (d, 1H), 7.80 (dd, 1H), 7.41 (d, 1H), 3.00-2.79 (m, 2H), 2.78-2.49 (m, 2H), 2.58 (s, 2H), 1.82-1.51 (m, 4H).

5.2 4-[6-(1-Methyl-1H-pyrazol-4-yl)pyridin-3-yl]-1-azabicyclo[2.2.1]heptane hydrochloride (2:1) (Compound No. 1)

0.055 g (0.26 mmol) of 4-(6-chloropyridin-3-yl)-1-azabicyclo[2.2.1]heptane obtained as in stage 5.1, in solution in 12 ml of a 1,2-dimethoxyethane/water 8/4 mixture, is introduced into a 100 ml round-bottomed flask. 0.137 g (0.66 mmol) of 1-methyl-4-(4,4,5,5-tetramethyl-1,3,2-dioxaborolan-2-yl)-1H-pyrazole, 0.091 g (0.66 mmol) of potassium carbonate and 0.028 g (0.04 mmol) of dichlorobis(triphenylphosphine)-palladium(II) are then successively introduced under an argon atmosphere. The mixture is heated at 110° C. for 2 hours, cooled to ambient temperature and poured into 300 ml of a saturated aqueous sodium carbonate solution. The aqueous phase is extracted twice with 100 ml of chloroform, and the combined organic phases are dried over sodium sulfate and concentrated under reduced pressure. The residue is purified by chromatography on a column of silica gel, elution being carried out with a mixture of chloroform, methanol and aqueous methanol in the proportions 90/10/1. The compound obtained in the base form (4-[6-(1-methyl-1H-pyrazol-4-yl)pyridin-3-yl]-1-azabicyclo[2.2.1]heptane) is converted to the hydrochloride by adding two equivalents of hydrochloric acid in solution (5-6 N) in isopropyl alcohol. After triturating from diethyl ether, 0.053 g (62%) of the expected product is obtained in the form of a white powder.

Melting point: 281-283° C.

$^1$H NMR ($d_6$-DMSO): δ (ppm): 8.67 (s, 1H), 8.55 (d, 1H), 8.35 (s, 1H), 8.22 (d, 1H), 8.04 (d, 1H), 3.90 (s, 3H), 3.60 (s, 2H), 3.55-3.31 (m, 4H), 2.31-2.07 (m, 4H).

EXAMPLE 6

Compound No. 13

4-[6-(4-Benzylpiperazin-1-yl)pyridin-3-yl]-1-azabicyclo[2.2.1]heptane 0.055 g (0.32 mmol) of 1-benzylpiperazine is introduced into a 50 ml round-bottomed flask under argon comprising 0.036 g (0.37 mmol) of sodium tert-butoxide in solution in 5 ml of toluene through which argon has been bubbled beforehand. 0.06 g (0.29 mmol) of 4-(6-chloropyridin-3-yl)-1-azabicyclo[2.2.1]heptane obtained in stage 5.1 of Example 5, 0.003 g (0.01 mmol) of palladium(II) acetate and 0.011 g (0.03 mmol) of 2-dicyclohexylphosphino-2'-(N,N-dimethylamino)biphenyl are then successively added under an argon atmosphere. The mixture is heated at 100° C. for 3 hours, cooled to ambient temperature, diluted with 40 ml of dichloromethane and poured into 300 ml of a saturated aqueous sodium carbonate solution. The aqueous phase is extracted twice with 100 ml of dichloromethane, and the combined organic phases are dried over sodium sulfate and concentrated under reduced pressure. The residue is purified by chromatography on a column of silica gel, elution being carried out with a mixture of chloroform, methanol and aqueous ammonia in the proportions 90/10/1. 0.04 g of the expected product is obtained in the form of a beige powder.

Melting point: 109-111° C.

$^1$H NMR ($d_6$-DMSO): δ (ppm): 8.05 (d, 1H), 7.49 (dd, 1H), 7.38-7.15 (m, 5H), 6.73 (d, 1H), 3.50 (s, 2H), 3.40 (br t, 4H), 3.01-2.79 (m, 2H), 2.69-2.35 (m, 8H), 1.78-1.42 (m, 4H).

EXAMPLE 7

Compound No. 29

4-(6-(Pyrroldin-1-yl)pyridin-3-yl)-1-azabicyclo[2.2.1]heptane 0.852 g (11.98 mmol) of pyrrolidine is added to a sealed tube comprising 0.060 g (0.29 mmol) of 4-(6-chloropyridin-3-yl)-1-azabicyclo[2.2.1]heptane obtained in stage 5.1 of Example 5. The mixture is heated at 130° C. for 3 hours, cooled to ambient temperature and diluted with 40 ml of toluene and the combined mixture is concentrated under reduced pressure. The residue thus obtained is diluted with 50 ml of dichloromethane and poured into 300 ml of a saturated aqueous sodium carbonate solution. The aqueous phase is extracted twice with 100 ml of dichloromethane, and the combined organic phases are dried over sodium sulfate and concentrated under reduced pressure. The residue is purified by chromatography on a column of silica gel, elution being carried out with a mixture of chloroform, methanol and aqueous ammonia in the proportions 85/15/1.5. 0.029 g of the expected product is obtained in the form of a brown powder.

Melting point: 119-121° C.

$^1$H NMR ($d_6$-DMSO): δ (ppm): 7.99 (d, 1H), 7.42 (dd, 1H), 6.35 (d, 1H), 3.43-3.18 (m, 6H), 2.96-2.78 (m, 2H), 2.62-2.44 (m, 2H), 2.00-1.82 (m, 4H), 1.75-1.41 (m, 4H).

EXAMPLE 8

Compound No. 62

4-[6-(Thiazol-2-yl)pyridin-3-yl]-1-azabicyclo[2.2.1]heptane 0.246 g (0.66 mmol) of 2-tributylstannylthiazole and 0.055 g (0.08 mmol) of bis(triphenylphosphine)palladium(II) chloride are successively introduced under argon into a 50 ml round-bottomed flask comprising 0.055 g (0.26 mmol) of 4-(6-chloropyridin-3-yl)-1-azabicyclo[2.2.1]heptane obtained in stage 5.1 of Example 5 in solution in 10 ml of tetrahydrofuran. The mixture is heated at reflux for 12 hours, cooled to ambient temperature, diluted with 40 ml of dichloromethane and poured into 300 ml of a saturated aqueous ammonium chloride solution. The aqueous phase is adjusted to pH=5 with a 1N hydrochloric acid solution. The organic phase is separated and then the aqueous phase is adjusted to pH=10 with sodium carbonate powder. The aqueous phase is extracted twice with 100 ml of dichloromethane, and the combined organic phases are dried over sodium sulfate and concentrated under reduced pressure. The residue is purified by chromatography on a column of silica gel, elution being carried out with a mixture of chloroform, methanol and aqueous ammonia in the proportions 95/5/0.5.

0.038 g of the expected product is obtained in the form of a white powder.

Melting point: 127-129° C.

$^1$H NMR (d$_6$-DMSO): δ (ppm): 8.60 (d, 1H), 8.04 (d, 1H), 7.98-7.82 (m, 2H), 7.77 (d, 1H), 3.02-2.76 (m, 2H), 2.70-2.33 (m, 4H), 1.90-1.51 (m, 4H).

The chemical structures and the physical properties of some examples of compounds according to the invention are illustrated in the following Table 1. In the "Salt" column of this table, "—" denotes a compound in the base state, "HBr" denotes a hydrobromide and "HCl" denotes a hydrochloride. The acid:base molar ratios are shown opposite. "BOC" denotes a t-butyloxycarbonyl group.

TABLE 1

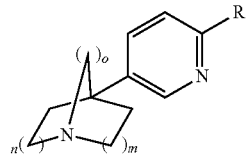

(I)

| No. | n | m | o | R | Salt | M.p. (° C.) (Melting point) |
|---|---|---|---|---|---|---|
| 1 | 1 | 1 | 1 | 1-methyl-1H-pyrazol-4-yl | HCl 2:1 | 281-283 |
| 2 | 2 | 2 | 1 | 1-methyl-1H-pyrazol-4-yl | HCl 2:1 | 271-273 |
| 3 | 2 | 2 | 1 | 3,4-dimethoxyphenyl | HCl 2:1 | 235-236 |
| 4 | 2 | 2 | 1 | OH | — | 191-192 |
| 5 | 2 | 2 | 1 | Cl | — | 245-246 |
| 6 | 1 | 1 | 1 | 1-methyl-1H-indol-5-yl | — | 186-187 |
| 7 | 2 | 2 | 1 | pyridin-4-yl | — | 134-136 |
| 8 | 1 | 1 | 1 | 4-fluorophenyl | — | 147-149 |
| 9 | 1 | 1 | 1 | 1-benzofur-2-yl | — | 164-165 |
| 10 | 2 | 2 | 1 | 1-benzofur-2-yl | — | 152-154 |
| 11 | 1 | 1 | 1 | pyridin-4-yl | — | 254-256 |
| 12 | 1 | 1 | 1 | quinolin-6-yl | HCl 2:1 | 327-328 |
| 13 | 1 | 1 | 1 | 4-benzylpiperazin-1-yl | — | 109-111 |
| 14 | 1 | 1 | 1 | 1-benzothien-2-yl | — | 202-203 |
| 15 | 1 | 1 | 1 | OH | — | 170-172 |
| 16 | 1 | 1 | 1 | 1,3-benzodioxol-5-yl | — | 256-258 |
| 17 | 1 | 1 | 1 | 3,4-dimethoxyphenyl | HCl 2:1 | 247-249 |
| 18 | 1 | 1 | 1 | 3-(trifluoromethyl)phenyl | HCl 2:1 | 191-192 |
| 19 | 1 | 1 | 1 | 3-fluorophenyl | — | 88-90 |
| 20 | 2 | 2 | 1 | 3-fluorophenyl | — | 102-104 |
| 21 | 1 | 1 | 1 | 3-furyl | — | 279-281 |
| 22 | 1 | 1 | 1 | dibenzo[b,d]fur-4-yl | — | 158-160 |
| 23 | 1 | 1 | 1 | quinolin-3-yl | — | 267-268 |
| 24 | 1 | 1 | 1 | pyridin-3-yl | — | 228-229 |
| 25 | 1 | 1 | 1 | 4-(trifluoromethoxy)phenyl | — | 75-76 |
| 26 | 2 | 2 | 1 | 1-benzothien-2-yl | — | 176-178 |
| 27 | 1 | 1 | 1 | 4-fluoro-2-methoxyphenyl | — | 169-170 |
| 28 | 1 | 1 | 1 | 1H-pyrrol-3-yl | HCl 2:1 | 324-326 |
| 29 | 1 | 1 | 1 | pyrrolidin-1-yl | — | 119-121 |
| 30 | 2 | 2 | 1 | dibenzo[b,d]fur-4-yl | — | 142-144 |
| 31 | 2 | 2 | 1 | 1,3-benzodioxol-5-yl | — | 124-126 |
| 32 | 2 | 2 | 1 | quinolin-6-yl | — | 151-153 |
| 33 | 2 | 2 | 1 | 1-methyl-1H-indol-5-yl | — | 166-168 |
| 34 | 2 | 2 | 1 | 1H-pyrrol-3-yl | — | 152-154 |
| 35 | 2 | 2 | 1 | 3-(trifluoromethyl)phenyl | HBr 2:1 | 155-157 |
| 36 | 2 | 2 | 1 | 4-fluorophenyl | — | 107-109 |
| 37 | 1 | 1 | 1 | pyrimidin-5-yl | — | 244-246 |
| 38 | 1 | 1 | 1 | 2,4-dimethoxypyrimidin-5-yl | — | 104-106 |
| 39 | 2 | 2 | 1 | biphenyl-4-yl | — | 146-148 |
| 40 | 2 | 2 | 1 | 3-furyl | — | 335-337 |
| 41 | 2 | 2 | 1 | pyridin-3-yl | — | 118-120 |
| 42 | 2 | 2 | 1 | 4-(trifluoromethoxy)phenyl | — | 120-122 |
| 43 | 2 | 2 | 1 | 4-fluoro-2-methoxyphenyl | — | 148-150 |
| 44 | 2 | 2 | 1 | quinolin-3-yl | — | 160-162 |
| 45 | 1 | 1 | 1 | biphenyl-4-yl | — | 191-192 |
| 46 | 1 | 1 | 1 | quinolin-8-yl | — | 176-178 |
| 47 | 2 | 2 | 1 | 1H-1,2,3-benzotriazol-1-yl | HCl 1:1 | 258-260 |
| 48 | 2 | 2 | 1 | dibenzo[b,d]thien-2-yl | HCl 2:1 | 242-244 |
| 49 | 2 | 2 | 1 | 4-methoxyphenyl | — | 138-139 |
| 50 | 2 | 2 | 1 | 3-methoxyphenyl | HCl 2:1 | 267-269 |
| 51 | 1 | 1 | 1 | 2,1,3-benzoxadiazol-5-yl | — | 139-140 |
| 52 | 1 | 1 | 1 | 2-(morpholin-4-yl)pyrimidin-5-yl | — | 226-227 |
| 53 | 1 | 1 | 1 | 1-methyl-1H-pyrrol-2-yl | HCl 2:1 | 248-250 |
| 54 | 1 | 1 | 1 | 3-fluoro-5-methoxyphenyl | — | 95-97 |
| 55 | 1 | 1 | 1 | 3-fluoro-4-methoxyphenyl | — | 125-126 |
| 56 | 1 | 1 | 1 | 2-fluoro-3-methoxyphenyl | — | 144-146 |
| 57 | 2 | 2 | 1 | 3-fluoro-4-methoxyphenyl | — | 138-140 |
| 58 | 2 | 2 | 1 | 2-fluoro-3-methoxyphenyl | — | 144-146 |
| 59 | 2 | 2 | 1 | 1-methyl-1H-pyrrol-2-yl | — | 105-107 |
| 60 | 2 | 2 | 1 | 2-furyl | HCl 2:1 | 292-294 |
| 61 | 2 | 2 | 1 | 3-(1H-pyrazol-1-yl)phenyl | — | 135-137 |
| 62 | 1 | 1 | 1 | thiazol-2-yl | — | 127-129 |
| 63 | 2 | 2 | 1 | pyrimidin-5-yl | — | 139-141 |
| 64 | 2 | 2 | 1 | 1-naphthyl | — | 167-169 |
| 65 | 2 | 2 | 1 | 2-(morpholin-4-yl)pyrimidin-5-yl | — | 189-191 |
| 66 | 2 | 2 | 1 | 2,4-dimethoxypyrimidin-5-yl | — | 81-83 |
| 67 | 2 | 2 | 1 | 2,1,3-benzoxadiazol-5-yl | — | 151-153 |
| 68 | 2 | 2 | 1 | phenyl | — | 103-105 |
| 69 | 2 | 2 | 1 | 2,5-dimethoxyphenyl | — | 101-103 |
| 70 | 2 | 2 | 1 | 4-(trifluoromethyl)phenyl | — | 135-137 |
| 71 | 2 | 2 | 1 | 6-methoxyphenyl-3-yl | — | 134-136 |
| 72 | 2 | 2 | 1 | isoquinolin-4-yl | HBr 2:1 | 332-334 |
| 73 | 2 | 2 | 1 | 3,5-bis(trifluoromethyl)phenyl | HBr 2:1 | 226-228 |
| 74 | 2 | 2 | 1 | thiazol-2-yl | — | 124-126 |
| 75 | 2 | 2 | 1 | 4-phenoxyphenyl | — | 129-131 |
| 76 | 2 | 2 | 1 | 2-fluorophenyl | — | 117-119 |
| 77 | 2 | 2 | 1 | (4-N-pyrrolidine)pyridin-3-yl | — | 301-303 |

TABLE 1-continued (I)

| No. | n | m | o | R | Salt | M.p. (° C.) (Melting point) |
|---|---|---|---|---|---|---|
| 78 | 2 | 2 | 1 | (N-(N'-BOC)piperazine)-pyridin-3-yl | — | 202-204 |
| 79 | 2 | 2 | 1 | 2-methoxyphenyl | HBr 2:1 | 239-241 |
| 80 | 2 | 2 | 1 | 2,4-dimethoxyphenyl | HBr 2:1 | 198-200 |
| 81 | 2 | 2 | 1 | 3-(trifluoromethoxy)phenyl | HBr 2:1 | 267-269 |
| 82 | 2 | 2 | 1 | 3-(N,N-dimethylamino)phenyl | HBr 3:1 | 256-258 |
| 83 | 1 | 1 | 1 | isoquinolin-4-yl | — | 143-145 |
| 84 | 1 | 1 | 1 | isoquinolin-5-yl | — | 176-178 |
| 85 | 1 | 1 | 1 | phenyl | — | 126-128 |
| 86 | 1 | 1 | 1 | 3,5-bis(trifluoromethyl)phenyl | — | 117-119 |
| 87 | 1 | 1 | 1 | 6-methoxypyridin-3-yl | — | 97-99 |
| 88 | 1 | 1 | 1 | (N-(N'-BOC)piperazine)-pyridin-3-yl | — | 216-218 |
| 89 | 2 | 2 | 1 | isoquinolin-5-yl | HBr 3:1 | 246-248 |
| 90 | 1 | 1 | 1 | 4-fluoropyridin-3-yl | — | 108-109 |
| 91 | 2 | 2 | 1 | 2-fluoropyridin-3-yl | — | 98-99 |
| 92 | 1 | 1 | 1 | 2-methoxyphenyl | HBr 2:1 | 114-116 |
| 93 | 1 | 1 | 1 | 2,4-dimethoxyphenyl | HBr 2:1 | 195-197 |
| 94 | 1 | 1 | 1 | 2,5-dimethoxyphenyl | HBr 2:1 | 152-154 |
| 95 | 1 | 1 | 1 | 2-fluorophenyl | — | 110-112 |
| 96 | 1 | 1 | 1 | 4-methoxyphenyl | — | 160-162 |
| 97 | 1 | 1 | 1 | 2-naphthyl | — | 154-156 |
| 98 | 1 | 1 | 1 | 4-phenoxyphenyl | — | 141-143 |
| 99 | 1 | 1 | 1 | 2-(trifluoromethyl)phenyl | HBr 2:1 | 310-312 |
| 100 | 2 | 2 | 1 | 2-naphthyl | — | 163-165 |
| 101 | 1 | 1 | 1 | 2-fluoropyridin-3-yl | — | 116-117 |
| 102 | 2 | 2 | 1 | 4-fluoropyridin-3-yl | — | 121-122 |
| 103 | 1 | 1 | 1 | 3-(trifluoromethoxy)phenyl | HCl 1:1 | 152-154 |
| 104 | 2 | 2 | 1 | quinolin-5-yl | — | 147-149 |
| 105 | 2 | 2 | 1 | 2-fluorobiphenyl-4-yl | — | 144 |
| 106 | 2 | 2 | 1 | 3-acetylphenyl | HBr 2:1 | 284-285 |
| 107 | 1 | 1 | 1 | 3-acetylphenyl | — | 95-98 |
| 108 | 1 | 1 | 1 | 3-methylphenyl | — | 134-136 |
| 109 | 1 | 1 | 1 | 2-fluorobiphenyl-4-yl | — | 153-155 |
| 110 | 1 | 1 | 1 | quinolin-5-yl | — | 129-131 |
| 111 | 1 | 1 | 1 | 3-methoxyphenyl | — | 87-89 |
| 112 | 1 | 1 | 1 | 3,4-difluorophenyl | — | 85-87 |
| 113 | 1 | 1 | 1 | 3-(pyrazol-1-yl)phenyl | — | 114-116 |

The compounds of the invention have formed the subject of pharmacological tests which have demonstrated their advantage as active substances of medicaments.

Thus, they have been studied with regard to their affinity with respect to nicotinic receptors comprising the $\alpha_7$ subunit according to the methods described by Mark and Collins in *J. Pharmacol. Exp. Ther.*, 1982, 22, 564 and by Marks et al. in *Mol. Pharmacol.*, 1986, 30, 427.

Male OFA rats weighing 150 to 200 g are decapitated and the entire brain is quickly removed, homogenized using a POLYTRON™ mill in 15 volumes of a 0.32M sucrose solution at 4° C. and then centrifuged at 1000 G for 10 min. The pellet is removed and the supernatant is centrifuged at 8000 G for 20 min at 4° C. The pellet is recovered and is homogenized using a POLYTRON™ mill in 15 volumes of doubly-distilled water at 4° C. and is then centrifuged at 8000 G for 20 min. The pellet is removed and the supernatant and the layer of skin (buffy coat) are centrifuged at 40 000 G for 20 min. The pellet is recovered, is resuspended with 15 volumes of doubly-distilled water at 4° C. and is centrifuged a further time at 40 000 G for 20 min before being stored at −80° C.

On the day of the experiment, the tissue is slowly defrosted and is suspended in 5 volumes of buffer. 150 μl of this membrane suspension are preincubated at 37° C. for 30 min in darkness in the presence or in the absence of the test compound. The membranes are then incubated for 60 min at 37° C. in darkness in the presence of 50 μl of 1 nM [$^3$H]-α-bungarotoxin in a final volume of 250 μl of buffer HEPES 20 mM, polyethyleneimine 0.05%. The reaction is halted by filtration through Whatman GF/C™ filters pretreated for 3 h with 0.05% polyethyleneimine. The filters are rinsed with two times 5 ml of buffer at 4° C. and the radioactivity retained on each filter is measured by liquid scintigraphy. The non-specific binding in the presence of α-bungarotoxin at a final concentration of 1 μM is determined; the non-specific binding represents approximately 60% of the total binding recovered on the filter. The percentage of inhibition of the specific binding of [$^3$H]-α-bungarotoxin is determined for each concentration of compound studied and then the $IC_{50}$ value, the concentration of compound which inhibits 50% of the specific binding, is calculated.

The $IC_{50}$ values of the compounds of the invention with the greatest affinity lie between 0.001 and 1 μM.

The experimental data for some specific compounds are shown in the following Table 2.

TABLE 2

| Compound No. | $IC_{50}\ \alpha_7$ (nM) |
|---|---|
| 113 | 4.7 |
| 16 | 9.1 |
| 12 | 37.1 |
| 19 | 13.8 |

The compounds of the invention were also studied with regard to their affinity with respect to nicotinic receptors comprising the $\alpha_4\beta_2$ subunit according to the methods described by Anderson and Arneric in *Eur. J. Pharmacol.* 1994, 253, 261 and by Hall et al. in *Brain Res.*, 1993, 600, 127.

Male Sprague-Dawley rats weighing 150 to 200 g are decapitated and the entire brain is quickly removed, homogenized in 15 volumes of 0.32 M sucrose solution at 4° C. and then centrifuged at 1000 G for 10 min. The pellet is removed and the supernatant is centrifuged at 20 000 G for 20 min at 4° C. The pellet is recovered and is homogenized using a POLYTRON™ mill in 15 volumes of doubly-distilled water at 4° C. and is then centrifuged at 8000 G for 20 min. The pellet is removed and the supernatant and the layer of skin (buffy coat) are centrifuged at 40 000 G for 20 min. The pellet is recovered, is resuspended in 15 ml of doubly-distilled water and is centrifuged a further time at 40 000 G before being stored at −80° C.

On the day of the experiment, the tissue is slowly defrosted and is suspended in 3 volumes of buffer. 150 μl of this membrane suspension are incubated at 4° C. for 120 min in the presence of 100 μl of 1 nM [$^3$H]-cystisine in a final volume of 500 μl of buffer, in the presence or in the absence of test compound. The reaction is halted by filtration through Whatman GF/B™ filters pretreated with polyethyleneimine. The filters are rinsed with two times 5 ml of buffer at 4° C. and the radioactivity retained on the filter is measured by liquid scintigraphy. The non-specific binding in the presence of 10 μM (−)-nicotine is determined; the non-specific binding represents 75 to 85% of the total binding recovered on the filter. The percentage of inhibition of the specific binding of [$^3$H]-cytisine, at doses of 1 μM and 10 μM, is determined for each concentration of compound studied. The $IC_{50}$ value, the concentration of compound which inhibits 50% of the specific binding, is calculated for the compounds of the invention with greatest affinity.

The $IC_{50}$ values of the compounds of the invention with the greatest affinity lie between 0.001 and 1 µM.

The compounds of the invention were also studied with regard to their affinity with respect to ganglionic peripheral nicotinic receptors according to the method described by Houghtling et al. in *Mol. Pharmacol.*, 1995, 48, 280.

Bovine adrenal glands stored at −80° C. are defrosted, homogenized in 20° volumes of 50 mM Tris-HCl buffer at pH 7.4 and at 4° C. using a POLYTRON™ mill and then centrifuged at 35 000 G for 10 min. The supernatant is removed and the pellet is resuspended in 30 volumes of 50 mM Tris-HCl buffer at 4° C., and the suspension is rehomogenized before being recentrifuged at 35 000 G for 10 min. The final pellet is taken up in 10 volumes of Tris-HCl buffer at 4° C. 100 µl of membrane, i.e. 10 mg of fresh tissue, are incubated at 24° C. for 3 h in the presence of 50 µl of [$^3$H]-epibatidine at a final concentration of 0.66 nM in a final volume of 250 µl of buffer, in the presence or in the absence of test compound. The reaction is halted by dilution of the samples with 50 µM Tris-HCl buffer, pH 7.4, at 4° C. and then filtration is carried out through Whatman GF/C™ filters pretreated for 3 hours with 0.5% polyethyleneimine. The filters are rinsed twice with 5 ml of buffer and the radioactivity retained on the filter is measured by liquid scintigraphy. The non-specific binding is determined in the presence of (−)-nicotine at a final concentration of 2 mM; the non-specific binding represents 30 to 40% of the total binding recovered on the filter. For each concentration of product studied, the percentage of inhibition of the specific binding of [$^3$H]-epibatidine is determined and then the $IC_{50}$ value, the concentration of compound which inhibits 50% of the specific binding, is calculated.

The $IC_{50}$ values of the compounds of the invention lie between 0.001 and 1 µM.

The results obtained show that some compounds of the invention are selective ligands for the $\alpha_7$ subunit of the nicotinic receptor and that others are mixed $\alpha_4\beta_2$ and $\alpha_7$.

These results suggest the use of the compounds in the treatment or prevention of disorders related to dysfunctioning of nicotinic receptors, in particular in the central nervous system but also in the peripheral system.

These disorders comprise detrimental cognitive changes, more specifically detrimental memory changes (acquisition, consolidation and recall), but also attacks on attentional processes, and disorders of the executive functions related to Alzheimer's disease, to pathological ageing (age associated memory impairment, AAMI) or normal ageing (senile dementia), to Parkinsonian syndrome, to trisomy 21 (Down's syndrome), to psychiatric pathologies, in particular cognitive impairment associated with schizophrenia (CIAS) or post-traumatic stress disorder (PTSD), to Korsakoffs alcoholic syndrome, to vascular dementias (multiinfarct dementia, MDI) or to cranial traumas.

The compounds of the invention might also be of use in the treatment of motor disorders observed in Parkinson's disease or other neurological diseases, such as Huntington's chorea, Tourette's syndrome, tardive dyskinesia and hyperkinesia.

They might also exhibit a neuroprotective therapeutic activity with respect to anatomic histopathological attacks related to the abovementioned neurodegenerative diseases.

They might also be of use in the treatment of multiple sclerosis.

The compounds of the invention might also constitute a curative or symptomatic treatment of strokes and cerebral hypoxic episodes. They can be used in the case of psychiatric pathologies: schizophrenia (positive and/or negative symptoms), bipolar disorders, depression, anxiety, panic attacks, PTSD, attention deficit hyperactivity disorder (ADHD) or obsessive-compulsive behavior.

They might prevent symptoms due to weaning from tobacco, from alcohol or from various dependence-inducing substances, such as cocaine, LSD, cannabis or benzodiazepines.

They might be of use in the treatment of pain of various origins (including chronic, neuropathic or inflammatory pain).

Furthermore, the compounds of the invention might be used in the treatment of lower limb ischemia, lower limb arterial occlusive disease (PAD: peripheral arterial disease), cardiac ischemia (stable angina), myocardial infarction, cardiac insufficiency, skin healing deficiency in diabetic patients, varicose ulcers of venous insufficiency, or septic shock.

The compounds of the invention might also be used in the treatment of inflammatory processes of various origins, in particular inflammation relating to the central nervous system, pulmonary inflammation related to allergies or to asthma, periodontitis, sarcoidosis, pancreatitis, reperfusion injuries or rheumatoid arthritis.

The compounds of the invention might also be of use in the treatment of dermatological pathologies, such as psoriasis, and in the treatment of asthma.

The compounds of the invention might also be used in the treatment of ulcerative colitis.

The compounds according to the invention can thus be used in the preparation of medicaments, in particular of medicaments of use in the treatment or prevention of disorders related to a dysfunctioning of the nicotinic receptors, in particular the abovementioned disorders.

Thus, according to another of its aspects, the subject-matter of the invention is medicaments which comprise a compound of formula (I) or an addition salt of the latter with a pharmaceutically acceptable acid or also a hydrate or a solvate of the compound of formula (I).

These medicaments are employed therapeutically, in particular in the treatment or prevention of disorders related to a dysfunctioning of the nicotinic receptors, in particular the abovementioned disorders.

According to another of its aspects, the present invention relates to pharmaceutical compositions comprising, as active principle, a compound according to the invention. These pharmaceutical compositions comprise an effective dose of at least one compound according to the invention, or a pharmaceutically acceptable salt, a hydrate or a solvate of the said compound, and also at least one pharmaceutically acceptable excipient. The said excipients are chosen, according to the pharmaceutical form and the method of administration desired, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above or its optional salt, solvate or hydrate can be administered in unit administration form, as a mixture with conventional pharmaceutical excipients, to animals and human beings for the prophylaxis or treatment of the above disorders or diseases.

The appropriate unit administration forms comprise the forms by the oral route, such as tablets, soft or hard gelatin capsules, powders, granules and solutions or suspensions to be taken orally, the forms for sublingual, buccal, intratracheal, intraocular or intranasal administration, the forms for administration by inhalation, the forms for topical, transdermal, subcutaneous, intramuscular or intravenous administration, the forms for rectal administration and implants. Use may be made, for topical application, of the compounds according to the invention in creams, gels, ointments or lotions.

By way of example, a unit administration form of a compound according to the invention in the form of a tablet can comprise the following components:

| Compound according to the invention | 50.0 mg |
| --- | --- |
| Mannitol | 223.75 mg |
| Croscarmellose sodium | 6.0 mg |
| Maize starch | 15.0 mg |
| Hydroxypropyl methylcellulose | 2.25 mg |
| Magnesium stearate | 3.0 mg |

The said unit forms comprise a dose in order to make possible daily administration of 0.01 to 20 mg of active principle per kg of body weight, depending on the pharmaceutical formulation form.

There may be specific cases where higher or lower dosages are appropriate; such dosages do not depart from the scope of the invention. According to the usual practice, the dosage appropriate to each patient is determined by the physician according to the method of administration and the weight and the response of the said patient.

The present invention, according to another of its aspects, also relates to a method for the treatment of the pathologies indicated above which comprises the administration, to a patient, of an effective dose of a compound according to the invention or one of its pharmaceutically acceptable salts or its hydrates or its solvates.

What is claimed is:

1. A compound of the formula (I):

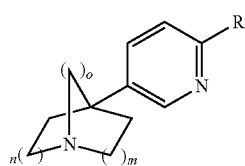

(I)

in which:
R represents hydrogen, halogen, hydroxyl, $(C_1-C_6)$alkoxy, $(C_3-C_7)$cycloalkyl-O—, $(C_3-C_7)$cycloalkyl-$(C_1-C_3)$alkylene-O—,
or a heterocycloalkyl, aryl or heteroaryl group; wherein said group is optionally substituted by one or more groups chosen from halogen, $(C_1-C_6)$alkyl, $(C_3-C_7)$cycloalkyl, $(C_3-C_7)$cycloalkyl-$(C_1-C_3)$alkylene, $(C_1-C_6)$alkoxy, $(C_3-C_7)$cycloalkyl-O—, $(C_3-C_7)$cycloalkyl-$(C_1-C_3)$alkylene-O—, $(C_1-C_6)$fluoroalkyl, $(C_1-C_6)$fluoroalkoxy, nitro, cyano, hydroxyl, amino, $(C_1-C_6)$alkylamino, di$(C_1-C_6)$alkylamino, heterocycloalkyl, aryl, aryl-$(C_1-C_6)$alkylene, heteroaryl, heteroaryl-$(C_1-C_6)$alkylene, aryl-O— or —C(O)—$(C_1-C_6)$alkyl groups, the heterocycloalkyl group optionally being substituted by —C(O)O(CH$_3$)$_3$;
n represents 2;
m represents 2; and
o represents 1;
or a salt thereof.

2. The compound of formula (I) according to claim 1, wherein:
R represents hydrogen, halogen, hydroxyl,
or a heterocycloalkyl, aryl or heteroaryl group; wherein said group is optionally substituted by one or more groups chosen from halogen, $(C_1-C_6)$alkyl, $(C_1-C_6)$alkoxy, $(C_1-C_6)$fluoroalkyl, $(C_1-C_6)$fluoroalkoxy, nitro, cyano, hydroxyl, amino, $(C_1-C_6)$alkylamino, di$(C_1-C_6)$alkylamino, heterocycloalkyl, aryl, aryl-$(C_1-C_6)$alkylene, heteroaryl, aryl-O— or —C(O)—$(C_1-C_6)$alkyl groups, the heterocycloalkyl group optionally being substituted by —C(O)O(CH$_3$)$_3$;
n represents 2;
m represents 2; and
o represents 1;
or a salt thereof.

3. The compound of formula (I) according to claim 1, wherein:
R represents halogen, hydroxyl,
or a heterocycloalkyl group or an aryl group or a heteroaryl group; wherein said group is optionally substituted by one or more groups chosen from halogen, $(C_1-C_6)$alkyl, $(C_1-C_6)$alkoxy, $(C_1-C_6)$fluoroalkyl, $(C_1-C_6)$fluoroalkoxy, di$(C_1-C_6)$alkylamino, heterocycloalkyl, aryl, aryl-$(C_1-C_6)$alkylene, heteroaryl, aryl-O— or —C(O)—$(C_1-C_6)$alkyl groups; the heterocycloalkyl group optionally being substituted by —C(O)O(CH$_3$)$_3$;
n represents 2;
m represents 2; and
o represents 1;
or a salt thereof.

4. The compound of formula (I) according to claim 1, wherein n and m are 2 and o is 1 or a salt thereof.

5. A pharmaceutical composition comprising a compound of formula (I) according to claim 1 or a pharmaceutically acceptable salt thereof and at least one pharmaceutically acceptable excipient.

6. A pharmaceutical composition comprising a compound of formula (I) according to claim 2 or a pharmaceutically acceptable salt thereof and at least one pharmaceutically acceptable excipient.

7. A pharmaceutical composition comprising a compound of formula (I) according to claim 3 or a pharmaceutically acceptable salt thereof and at least one pharmaceutically acceptable excipient.

8. A pharmaceutical composition comprising a compound of formula (I) according to claim 4 or a pharmaceutically acceptable salt thereof and at least one pharmaceutically acceptable excipient.

* * * * *